(12) United States Patent
Dolderer

(10) Patent No.: US 7,915,294 B2
(45) Date of Patent: Mar. 29, 2011

(54) METHOD OF TREATING COLORECTAL CARCINOMA

(76) Inventor: Juergen Dolderer, Tuebingen (DE)

( * ) Notice: Subject to any disclaimer, the term of this patent is extended or adjusted under 35 U.S.C. 154(b) by 0 days.

(21) Appl. No.: 12/369,102

(22) Filed: Feb. 11, 2009

(65) Prior Publication Data

US 2009/0192193 A1 Jul. 30, 2009

Related U.S. Application Data

(60) Continuation of application No. 10/516,521, filed on May 2, 2005, which is a division of application No. PCT/EP03/05710, filed on May 30, 2003, now Pat. No. 7,598,270.

(30) Foreign Application Priority Data

May 31, 2002 (DE) .................. 102 24 534

(51) Int. Cl.
*A61K 31/445* (2006.01)
*G01N 33/574* (2006.01)
(52) U.S. Cl. .................... 514/318; 435/7.23
(58) Field of Classification Search .............. 435/69.1
See application file for complete search history.

(56) References Cited

U.S. PATENT DOCUMENTS 6,071,720 A * 6/2000 Hillman et al. ............. 435/69.1

OTHER PUBLICATIONS

Bianchi et al., herg Encodes a K+ Current Highly Conserved in Tumors of Different Histogenesis: A Selective Advantage for Cancer Cells, Cancer Research, 1998, 58, p. 815-822.*
Wang et al., Modulation of HERG affinity for E-4031 by [K+] and C-type inactivation, FEBS Letters, 1997, 417, pp. 43-47.*
Cherubini et al: "HERG Potassium Channels Are More Frequently Expressed in Human Endometrial Cancer As Compared to Non-Cancerous Endometrium" Br.J. Cancer 2000, December 83(12):1722-9.

* cited by examiner

*Primary Examiner* — Frederick Krass
*Assistant Examiner* — Darryl C Sutton
(74) *Attorney, Agent, or Firm* — Jonathan Myers

(57) ABSTRACT

A method is disclosed for detecting colorectal carcinoma having at least one HERG potassium ion channel, where at least one HERG potassium channel is detected in a tissue biopsy of the human color or rectum. In addition, a method is disclosed for treating colorectal carcinoma having at least one HERG potassium channel in a patient in need of said treatment, which comprises the step of administering to said patient, a therapeutically effective amount of 4-[1-{2-(6-methyl-2-pyridinyl)ethyl-4-piperidinyl}carbonyl]methane-sulfoanilide 2HCl sufficient to treat the colorectal carcinoma having at least one HERG potassium channel by selectively blockading the HERG potassium channel.

3 Claims, 3 Drawing Sheets

RT-PCR for detecting CEA, CK-19, CK-20 and HERG mRNA expression in healthy colon tissue, in tubulovilious adenomas of the colon and in colorectal carcinomas.

Replication of Colo 205 cells in the presence of the HERG blocker E-4031.

Initial Inoculation: 10,000 cells per well.

Depicting the inhibition of proliferation of the Colo-205 colorectal carcinoma cell line by the selective inhibitor E-4031 of the HERG potassium channel.

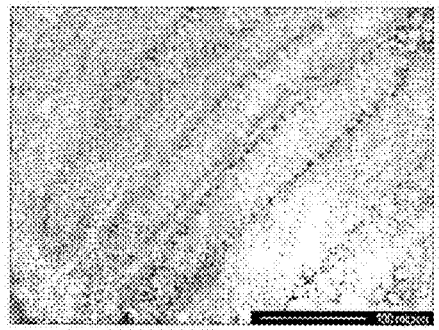
Figure 3

Figure 4

Figures 3 and 4: Immunohistochemically positive reaction of the anti-ERG1 (HERG) antibodi in colorectal cancer.

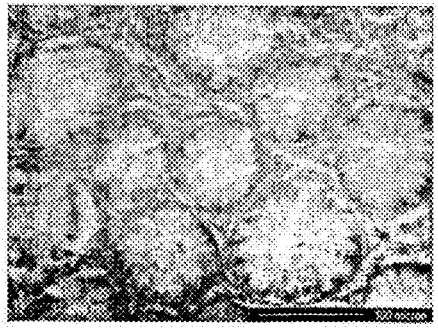
Figure 5

Immunohistochemically negative reaction in normal healthy colorectal tissue

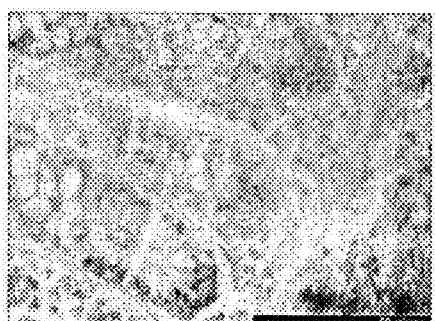
Figure 6

Immunohisochemically positive reaction in the histopathologically un-remarkable remaining intestinal specimen of the resected tissue of the tumor patient with later locoregional recurrence of the cancer

METHOD OF TREATING COLORECTAL CARCINOMA

CROSS REFERENCE TO RELATED APPLICATION

This application is a continuation of application Ser. No. 10/516,521 filed 2 May 2005, now U.S. Pat. No. 7,598,270, which is the US National Phase of PCT/EP03/05710 filed 30 May 2003, which itself claims the priority of German Application 102 24 534.7 filed 31 May 2002.

FIELD OF THE INVENTION

This invention relates to a diagnostic agent and a method for detection of cancer, in particular a method for detection of colorectal cancer (cancer of the large intestine) in a tissue biopsy of the human colon or rectum and a means for treatment of carcinoma, in particular colorectal carcinoma.

BACKGROUND OF THE INVENTION

Cancer is known to have become increasingly important in all countries. Treatment of cancer and therapeutic success depend to a significant extent on prompt detection of the cancer. Therefore, there is a great demand for reliable cancer diagnostic agents, in particular those that allow detection of metastases and micrometastases, even when there are no definite histological findings or when the histological findings are negative.

Colorectal cancer is the second main cause of cancer fatalities; the incidence has been increasing steadily and it often recurs after a curative surgical operation. Colorectal cancer (malignant tumors of the colon and rectum) are occurring in a constantly increasing incidence in industrial countries and constitute the second most common type of cancer in men and the third most common in women. Colorectal cancer constitutes 50% of malignancies. There are more than 200,000 new cases of colorectal cancer each year, and more than 100,000 patients die of it. Colorectal cancer is thus the second leading cause of death due to cancer.

Colorectal cancer may develop de novo or as part of an adenoma-carcinoma sequence in an adenomatous polyp. The probability of a malignancy is between 1% and 40% in the case of adenomas. To this extent, the patients with colorectal polyps constitute a risk group.

For this reason, early detection of colorectal cancer in adenomas and reliable differentiation from benign colorectal tissue are of crucial importance, especially for the prognosis and course of treatment.

Diagnosis and prognosis for this type of cancer are influenced by a variety of properties which are present at the time of the initial diagnosis. These factors include age, sex, duration of symptoms, condition of the intestinal obstruction, tumor localization, the need for a blood transfusion and the quality of the surgical intervention. Although a number of tumor properties such as vascular lymphatic invasiveness, the degree of differentiation and the preoperative titer of conventional tumor markers have shown a prognostic relevance, but there are no suitable markers for detection of early stages of cancer (benign colorectal precursors (adenomas) that become malignant) or for histopathologically unremarkable micrometastases (minimal residual disease) which may be responsible for a recurrence of the carcinoma, even after curative surgical resection. The tumor markers CEA, CK 19 and CK 20 which have been used in the past are indicative of the current prognosis but are unreliable in a differential diagnosis.

OBJECT OF THE INVENTION

Therefore, the object of this invention is to make available a reliable diagnostic agent and a method for detection of colorectal cancer and also to permit the use of an effective agent for treatment of colorectal cancer.

SUMMARY OF THE INVENTION

To achieve this object, this invention proposes that a tissue biopsy of the human colon or rectum should be tested for the presence of HERG potassium channels.

Therefore, the object of this invention is a diagnostic agent for detection of colorectal cancer with which the presence of at least one HERG potassium channel in a tissue specimen of the human colon or rectum, which is free of HERG potassium channels in a healthy person, can be detected. Another object of the present invention is a method for diagnosing colorectal cancer, whereby the presence of at least one HERG potassium channel is detected in a tissue biopsy of the human colon or rectum, which is free of HERG potassium channels in a healthy person, or in lymph nodes or in a body fluid.

Detection of a HERG potassium channel with the diagnostic agent according to the present invention is of course a reliable indication of the presence of colorectal cancer only if the detection is performed in a tissue biopsy of the human colon or rectum or in lymph nodes or in a body fluid which is free of HERG potassium channels in a healthy person. This does not apply to myocardial tissue or the brain, where HERG potassium channels always occur in a healthy person. However, if a HERG potassium channel is detected in a tissue biopsy of the colon or rectum, for example, which are known not to normally have HERG potassium channels, then this is a reliable detection of the presence of cancer.

Detection of cancer based on the occurrence of HERG potassium channels is reliable even if this detection is performed in a body fluid such as blood, blood plasma, blood serum, urine, perspiration or lacrimal fluid or feces in which HERG potassium channels normally never occur under normal conditions.

An example of the inventive method and diagnosing a cancer consists of diagnosing a colorectal cancer by detecting at least one HERG potassium channel in a tissue biopsy of the human colon.

For the diagnosis, a tissue biopsy of the colon and/or rectum is tested in the laboratory, with the HERG potassium channel being expressed in colorectal carcinoma cells which can be detected by the highly sensitive RT-PCR method as well as by the immunohistochemical tests that are widely used in clinical practice.

The surprising and valuable finding is that the HERG potassium channel is a highly selective functional tumor marker for colorectal carcinoma and thus can be used in diagnostics, especially for detection of early stages of cancer, for detection of unremarkable micrometastases and for differentiation from healthy colorectal tissue.

Members of the ether a-go-go (EAG) potassium channel family, in particular the eag-dependent gene product (eag-related gene; ERG) such as the human ERG (HERG) potassium channel are suitable for diagnostic purposes. They can be found in various tumor cell lines of varying histogenesis; it is known that they play a role in cell proliferation and transformation.

The reverse transcriptase polymerase chain reaction (RT-PCR) is a very efficient and highly sensitive method of detecting minimal tumor-associated mRNA transcription. Immunohistochemistry is a customary and widespread method in clinical practice and is therefore easy to integrate into routine techniques.

The HERG potassium channel (HERG=human eag-related gene) is a special type of human potassium channel which belongs to the eag (ether a-go-go) family of voltage-activated potassium channels. The HERG potassium channel evidently plays an important pathophysiological role in the regulatory mechanisms in neoplastic cells of varying histopathogenesis and triggers unlimited tumor growth.

The present invention proposes the use of the antiarrhythmic agent E-4031 for treatment of colorectal carcinoma cells. This is based on the valuable finding that the functional HERG potassium channel that plays an important role in cell proliferation and in carcinoma growth can be blocked selectively by the antiarrhythmic agent E-4031. This allows new approaches in cancer therapy.

Thus the invention is directed to a method of treating a colorectal carcinoma having at least one voltage-activated potassium ion channel HERG subunit in a patient in need of said treatment, which comprises the step of administering to said patient a therapeutically effective amount of 4-[1-{2-(6-methyl-2-pyridinyl)ethyl-4-piperidinyl}carbonyl]methane-sulfoanilide 2HCl sufficient to treat the colorectal carcinoma having at least one voltage-activated potassium ion channel HERG subunit. In particular the invention is directed to a method of treating colorectal carcinoma having at least one voltage-activated potassium ion channel HERG subunit in a patient in need of said treatment, which comprises the step of administering to said patient, a therapeutically effective amount of 4-[1-{2-(6-methyl-2-pyridinyl)ethyl-4-piperidinyl}carbonyl]methane-sulfoanilide 2HCl sufficient to treat the colorectal carcinoma having at least one voltage-activated potassium ion channel HERG subunit by selectively blockading the HERG subunit.

The antiarrhythmic agent E-4031 is a 4-[1-[2-(6-methyl-2-pyridinyl)ethyl-4-piperidinyl]carbonyl]methanesulfoanilide. 2HCl of the following formula:

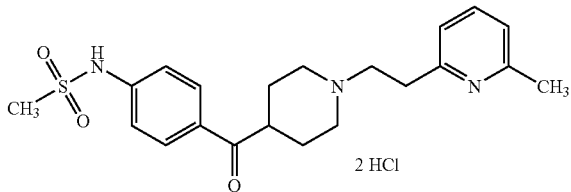

BRIEF DESCRIPTION OF THE DRAWINGS

FIGS. 3 and 4 show a staining pattern indicating an immunohistochemically positive reaction of the anti-ERG1 (HERG) antibody in colorectal cancer.

FIG. 5 shows an immunohistochemically negative reaction in normal healthy colorectal tissue.

FIG. 6 shows a weak immunohistochemically positive reaction for basal epithelial cells in the histopathologically unremarkable remaining intestinal specimen of the resected tissue of a tumor patient with later locoregional recurrence of the cancer.

Figure 1:
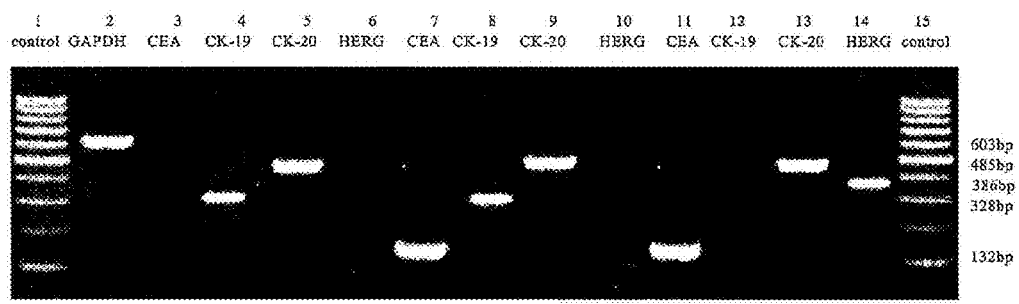
FIG. 1 is a showing RT/PCR amplification for detecting CEA, CK-19, CK-20 and HERG mRNA expression in healthy colon tissue, in tubulovillous adenocarcinomas of the colon, and in colorectal carcinoma.

Tests were performed on 24 tissue biopsies from 18 different patients (twelve women and six men between the ages of 51 and 86, average age 67.7 years) with colorectal cancer of UICC classifications I through IV. Five cancers were located in the colon, four were located in the sigmoid colon and nine were located in the rectum. The tissue biopsies were excised from the surrounding tissue to prevent cross-contamination. A new scalpel was used for each individual tissue biopsy.

The clinical and histopathological UICC classification as well as the Dukes' classification of patients with colorectal adenocarcinoma yielded the following result:
Stage I—Duke A: 3 (pT1=1, pT2=2)
Stage III—Duke B: 5 (pT3=5, pT4=0)
Stage III—Duke C: =7 (pN1=4, pN2=3)
Stage IV—Duke D: 3 (pM1=3)

Histopathologically negative biopsies of colon tissue of seven patients (four women and three men between the ages of 60 and 68, average age 62.8), three of which were from a tubulovillous adenoma of the colon and four of which were from a sigmoid diverticulitis were used as the negative controls (Table 2).

The histopathological diagnoses, UICC classification and Dukes' classification as well as the TNM classification were performed under standardized conditions. The tissue biopsy was deep-frozen in liquid nitrogen immediately after excision and stored at −80° C. until RNA extraction.

All the cellular RNA isolation from the frozen tissue biopsy was performed using the Qiagen RNeasy mini-kit according to the manufacturer's instructions (Hilden, Germany). The amount and purity of the RNA were determined by spectrophotometry at wavelengths of 260 nm and 280 nm.

The Colo-205 colorectal carcinoma cell line was used as a positive control for detecting the sensitivity of these experiments.

Reverse Transcription

The cDNA was synthesized from 2 µg total RNA in a volume of 20 µL reaction mixture containing 4 µL of 5× reaction buffer (50 mmol/L Tris-HCl, pH 8.3, 75 mmol/L KCl and 3 mmol/L MgCl$_2$), 500 µmol/L DNTP, 100 µrnol/L solution of poly-dT15 primer (Roche Diagnostic, Mannheim, Germany) and 500 units of Superscript II (Gibco BRL, Gaithersburg, Md., USA). The mixture was incubated for 60 minutes at 42° C., then heated for two minutes at 90° C. and next cooled on ice.

Primer sequences for the RT-PCR analysis:
The following primer sequences were used for the subsequent RT-PCR tests:
The primer sequences for CEA mRNA were:
A. 5'-TCTGGAACTTCTCCTGGTTCTCTCAGCTGG-3' (SEQ ID NO:1) for the outer sense;
B. 5'-TGTAGCTGTTGCAAATGCTTTAAGGAAGAA-3' (SEQ ID NO:2) for the antisense; and
C. 5'-GGGCCACTGTCGGCATCATGATTGG-3' (SEQ ID NO:3) for the inner sense cases.

The primer sequences for CK-19 mRNA were:
A. 5'-GTGGAGGTGGATTCCGCTCC-3' (SEQ ID NO:4) for the outer sense;
B. 5'-TGGCAATCTCCTGCTCCAG-3' (SEQ ID NO:5) for the outer antisense;
C. 5'-ATGGCCGAGCAGAACCGGAA-3' (SEQ ID NO:6) for the inner sense; and
D. 5'-CCATGAGCCGCTGGTACTCC-3' (SEQ ID NO: 7) for the inner antisense cases.

The primer sequences for CK-20 mRNA were:
A. 5'-GCGTTTATGGGGGTGCTGGAG-3' (SEQ ID NO:8) for the outer sense;
B. 5'-AAGGCTCTGGGAGGTGCGTCTC-3' (SEQ ID NO:9) for the outer antisense;
C. 5'-CGGCGGGGACCTGTTTGT-3' (SEQ ID NO: 10) for the inner sense; and
D. 5'-CAGTGTTGCCCAGATGCTTGTG-3' (SEQ ID NO: 11) for the inner antisense cases.

The primer sequences for the HERG mRNA were:
A. primer up 5'-AGCTGATCGGGCTGCTGAAGACTG-3' (SEQ ID NO:12) and
B. primer down 5'-AATGAGCATGACGCAGATG-GAGAAG-3' (SEQ ID NO:13).

To investigate the integrity of the extracted RNA and to ensure that equimolar RNA was used, the extracted RNA was tested with glyceraldehyde-3-phosphate dehydrogenase (GAPDH) by RT-PCR. The primary sequences for GAPDH were:
5'-CCACCCATGGCAAATTCCATGGCA-3' (SEQ ID NO:14) sense and
5'-TCTAGACGGCAGGTCAGGTCCACC-3' (SEQ ID NO:15) antisense primers.

Reverse transcriptase polymerase chain reaction (RT•PCR):

Two-step RT-PCR was used for amplification of cDNA of CEA, CK-19 and CK-20 as well as HERG.

PCR was performed as follows: PCR was performed in a volume of 50 µL and 2 µg of the total RNA per sample. For the first PCR round, 2 µL, aliquots of the cDNA solution were mixed with 10.5 µL of the PCR reaction mixture containing 1.25 µL 10×PCR buffer (10 mmol/L Tris-HCl, pH 8.3, 50 mmol/L KCl and 1.5 mmol/l $MgCl_2$), 200 µmol/L DNTP, 0.5 µmol/L of each primer and 2.5 units of platinum Taq polymerase (Gibco BRL, Gaithersburg, Md.).

The reaction was continued in a PCR Thermocycler (Biometra, Gottinqen, Germany). For CEA, CK-19 and CK-20 amplification, the following conditions were used: activation of Taq polymerase for four minutes at 95° C., template denaturing for 45 seconds at 95° C., annealing for 45 seconds at 60° C. and elongation for 45 seconds at 72° C. for 20 cycles. HERG amplification was performed for four minutes at 95° C., for one minute at 55° C., for one minute at 72° C. and for one minute at 95° C. for 30 cycles. Two microliters of the first PCR product were transferred to a second tube and amplified further (CEA, CK-19 and CK-20: for four minutes at 95° C.; 45 sec at 95° C.; 45 sec at 60° C. and 45 sec at 72° C. in 20 cycles and HERG for four minutes at 95° C.; one minute at 55° C.; one minute at 72° C. and one minute at 95° C. in 30 cycles). All pipetting work was performed on ice while working at a sterile workbench and then the tubes were placed in the Thermocycler. First however, they were heated to the denaturing temperature before amplification was started.

The amplified DNA fragments were 132 base pairs (bp) for CEA primer pairs, 328 base pairs for CK-19 primer pairs, 485 base pairs for CD-20 primer pairs and 386 base pairs for HERG primer pairs. Each tissue biopsy was tested at least twice.

To check on the integrity for cDNA, amplification for GAPDH was performed in 25 cycles with 603 base pairs of the cDNA fragments (four minutes at 95° C.; 45 sec at 95° C.; 45 sec at 60° C.; and 45 sec at 72° C.).

The PCR products were applied to a 2% agarose gel and stained with ethidium bromide.

Sensitivity Tests of the RT-PCR Method

The Colo-205 colorectal cancer cell line was used as a positive control for the detection sensitivity in these experiments. To determine the sensitivity of the method, dilution series of $10^6$ to $10^0$ colorectal carcinoma cells (CoI0-205) were prepared and then $10^7$ lymphocytes from healthy donors were added. RT-PCR was performed after extraction of the total RNA. The dilution series of the RNA showed that the primers were capable of detecting a quantity of mRNA equivalent to one tumor cell in $10^6$ lymphocytes.

Immunohistochemistry

Biopsies of colorectal carcinomas and healthy colorectal tissue were fixed in buffered formalin and embedded in paraffin. The histology was evaluated on sections stained with hematoxylin and eosin. Additional sections were used for the immunohistochemical verification.

For the immunohistochemistry of the anti-HERG antibody, a protocol of the ABC (avidin-biotin-peroxidase complex) detection method was used.

After applying the sections to microscope slides and air drying them overnight at 37° C., deparaffinization was performed with xylene and rehydration was performed with a descending alcohol series. The endogenous peroxidase was blocked by immersion of the sections for ten minutes in a solution of 19 mL phosphate buffer, 1 mL methanol and 200 µL 30% $H_2O_2$. Then the sections were rinsed with PBS 6×10 min.

To reduce the nonspecific antibody binding, the sections were preincubated with normal goat serum.

Then the sections were incubated for one hour at 4° C. with rabbit anti-ERG1 (HERG) (AB5222-200UL, Chemicon, Temecula, Calif., USA) as the primary antibody in a 1:500 dilution. After rinsing three times with PBS, the sections were incubated in biotinylated anti-rabbit antibody (Vector) in a dilution of 1:200 for one hour at 25° C. Then the sections were rinsed three times with PBS. Next they were incubated with the ABC complex (Vector) for one hour at 25° C. After rinsing several times, the sections were treated with 3,3'-diaminobenzidine tetrahydrochloride (DAB) (Sigma) for three minutes at 25° C. according to a standard protocol (0.05% DAB in 0.1 M phosphate buffer and 0.3% $H_2O_2$) for visualization of the primary antibody.

The staining of the sections was compared under a microscope. The staining reaction was stopped by rinsing with PBS.

When a positive antibody reaction was obtained, the affected tissue area was stained brown homogeneously.

After immunohistochemistry, the sections were dried overnight, dehydrated and then covered.

Negative controls: same procedure without primary antibody. Positive controls: experiments with anti-ERG1 (HERG) antibody were performed on sections of human heart.

Proliferation test on the Colo-205 colorectal carcinoma cell line with E-4031

Proliferation tests (growth experiments) were performed with the 3-(4,5-dimethylthiazol-2-yl)-2,5-diphenyl-2H-tetrazolium bromide MTT test. Cells of the Colo-205 colorectal carcinoma cell line were harvested with 0.05% EDTA and then counted. The cells were then sown in a 96-well plate with $10^4$ live cells per well and left for 24 hours to adhere. After 24 hours, the medium was exchanged with E-4031 in various concentrations of 1 μm, 5 μM and 10 μM. The final volume was 200 μL per well. After incubating for 0 to 7 days, 20 μL MTT (5 mg/mL in PBS) was added and incubated for two hours at 37° C. The medium was then removed and 100 dimethyl sulfoxide (Sigma, Germany) was placed in each well for ten minutes.

A 96-well microtiter plate reader (Comtek, Germany) was used for the analysis. At a wavelength of 570 nm angstrom the MTT test was read in the ELLSA microtiter plate reader. The average concentration in a set of five wells was measured.

The absorption of the untreated controls was assumed to be 100% and the $IC_{50}$ was calculated accordingly.

Statistical Analysis

A difference of P<0.05 was assumed to be significant.

Results of RT-PCR

CEA, CK-19 and CK-20 were expressed in the carcinoma, in the control tissue and in the Colo-205 colorectal cell line.

columns 7 through 10 were obtained on a tissue biopsy of a patient with a tubulovillous adenoma of the colon (patient no. 1 in Table 2). The bands in columns 11 through 14 represent a tissue biopsy of patient with a colorectal carcinoma (patient no. 3 in Table 1). The DNA fragments are applied to a 2% agarose gel and stained with ethidium bromide.

As summarized in Table 1, CEA can be detected in 22 (91.7%) tissue biopsies of colorectal carcinomas (of 18 different patients tested), CK-19 can be detected in 19 tissue biopsies (79.2%), CK-20 in 23 tissue biopsies (95.8%) and HERG alone can be detected in 100% i.e., all 24 tissue biopsies.

In all samples, except for CK-19 and CD-20 expression in patient no. 2, there were no differences in the mRNA results of the various tissue biopsies from the same test preparation (patients nos. 4, 6, 7, 8, 9) (Table 1).

TABLE 1

Detection of mRNA expression of tumor markers CEA, CK-19, CK-20 and HERG by RT-PCR in colorectal carcinomas

| Patient | GAPDH | CEA | CK-19 | CK-20 | HERG | Staging TNM | Localization |
|---|---|---|---|---|---|---|---|
| 1 | pos | pos | pos | pos | pos | III-T4, N1 (2/10), MO | Sigmoid |
| 2a | pos | pos | neg | pos | pos | III-T3, N1 (1/9), MO | Colon |
| 2b | pos | pos | pos | pos | pos | | |
| 3 | pos | pos | neg | pos | pos | II-T3, NO (0.15), MO | Colon |
| 4a | pos | pos | pos | pos | pos | IV-T3, N2 (25/27), M1 | Rectum |
| 4b | pos | pos | pos | pos | pos | | |
| 5 | pos | neg | pos | pos | pos | III-T2, N1 (2/12), MO | Sigmoid |
| 6a | pos | pos | pos | pos | pos | III-T3, N1 (1/35), MO | Rectum |
| 6b | pos | pos | pos | pos | pos | | |
| 7a | pos | pos | neg | pos | pos | III-T3, N2 (21/27), MO | Rectum |
| 7b | pos | pos | neg | pos | pos | | |
| 8a | pos | pos | pos | pos | pos | I-T2, NO (0/10), MO | Colon |
| 8b | pos | pos | pos | pos | pos | | |
| 9a | pos | pos | pos | pos | pos | II-T3, NO (0.4), MO | Rectum |
| 9b | pos | pos | pos | pos | pos | | |
| 10 | pos | pos | pos | pos | pos | IV-T3, N2 (6/16), M1 | Rectum |
| 11 | pos | pos | pos | pos | pos | II-T3, NO (0/4), MO | Colon |
| 12 | pos | pos | pos | pos | pos | IV-T3, N2 (6/16), M1 | Sigmoid |
| 13 | pos | pos | pos | pos | pos | II-T3, NO (0/7), MO | Rectum |
| 14 | pos | pos | pos | pos | pos | II-T3, NO (0/13), MO | Colon |
| 15 | pos | pos | pos | pos | pos | III-T3, N2 (6/11), MO | Rectum |
| 16 | pos | pos | pos | pos | pos | I-T1, NO (0/16), MO | Sigmoid |
| 17 | pos | pos | pos | pos | pos | III-T3, N2 (6/36), MO | Rectum |
| 18 | pos | neg | neg | pos | pos | II-T3, NO (0/16), MO | Rectum |

HERG expression, however, was 100% limited to only the carcinoma tissue and the Colo-205 cells. As shown in FIG. 1 and Table 1, tissue biopsies which definitely show a colorectal carcinoma in the histopathological examination also showed expression of all markers (CEA, CK-19, CK-20 and HERG). Colorectal tissue from patients without a malignancy would also express CEA, CK-19 and/or CK-20, but no HERG could ever be detected (Table 2). When RT-PCR was performed without the RT enzyme, no bands could be detected in the Colo-205 cell line, which proves that no DNA was present and thus the RT-PCR conditions are adjusted very well.

In columns 1 and 15, FIG. 1 shows 100 base pair increments as control bands. Column 2 shows the GAPDH control which was positive in all samples. The results in columns 3 through 6 are from a tissue biopsy of a patient with sigmoid diverticulitis (patient no. 6 in Table 2) and the results in The grading (degree of histopathological differentiation) of the colorectal carcinomas was G2 for all tissue biopsies except the biopsy from patient no. 1 (G2-3), patient no. 4 (G3) and patient no. 9 (G2-3).

HERG mRNA was not detected in any (0%) of the histopathologically negative colorectal tissue biopsies of three patients with a tubulovillous adenoma of the colon and the four patients with sigmoid diverticulitis who served as negative controls (FIG. 1 and Table 2).

The mRNA of the tumor markers CEA, CK-19 and CK-20 was positive in all patients with an adenoma of the colon (100%). The mRNA of the markers CEA, CK-19 and CK-20 was positive in two patients (50%) in the tissue biopsies of the patients with sigmoid diverticulitis.

TABLE 2

Detection of mRNA expression of tumor markers CEA, CK-19, CK-20 and HERG by RT-PCR in histopathologically negative colorectal tissue.

| Patient | GAPDH | CEA | CK-19 | CK-20 | HERG | Histology | Localization |
|---|---|---|---|---|---|---|---|
| 1 | pos | pos | pos | pos | neg | tubulovillous adenoma | Colon |
| 2 | pos | pos | pos | pos | neg | tubulovillous adenoma | Colon |
| 3 | pos | pos | pos | pos | neg | tubulovillous adenoma | Colon |
| 4 | pos | pos | neg | neg | neg | sigmoid diverticulitis | Sigmoid |
| 5 | pos | pos | pos | pos | neg | sigmoid diverticulitis | Sigmoid |
| 6 | pos | neg | pos | pos | neg | sigmoid diverticulitis | Sigmoid |
| 7 | pos | neg | neg | neg | neg | sigmoid diverticulitis | Sigmoid |

Results of Immunohistochemistry

Results of immunohistochemical detection of the anti-ERG1 (HERG) antibody definitely show an immunohistochemically positive reaction by staining of the malignant (glandular) tissue components in question in all biopsies of the colorectal carcinoma (Table 3). The immune reactivity is limited to the basal part of the cytoplasm of the epithelial cells (FIGS. 3 and 4). In addition to epithelial cells, diffuse reactions can also be detected in the lamina propria and in the blood vessels (blood cells). In addition, isolated cells not characterized further are found in the muscle layers.

The remaining intestinal sections of the resected material from the same tumor patient that were histopathologically negative were also immunohistochemically negative in most tissue biopsies. However, in isolated cases of immunohistochemically positive tissue biopsies, a weak but definitely positive immune reaction was found in the basal epithelial cells at the base of the glands in the remaining sections of the resected intestine that were histopathologically negative (FIG. 6). In a representative number of patients, a locoregional recurrence of the carcinoma was detected within a period of two years after surgical resection of the colorectal carcinoma (patients nos. 19-25 in Table 3).

This sensitive and reliable immunohistochemical detection of HERG in histopathologically unremarkable tissue and thus the detection of micrometastases make HERG a reliable tumor marker.

In no case did the histopathologically negative colorectal tissue biopsies of benign intestinal changes (sigmoid diverticulitis, colorectal adenomas) or healthy colorectal tissue biopsies (regular healthy intestinal mucosa) show staining in any cases and thus they gave a negative immunohistochemical reaction (Table 4 and FIG. 5).

TABLE 3

Immunohistochemical results in the colorectal carcinoma tissue and in the histopathologically negative remaining colorectal tissue of the same tumor patient (of patients with continuous numbers 1 through 25, patients nos. 1 through 18 are included in PCR).

| Patient | Carcinoma tissue | Remaining intestine of the resected tissue histologically negative |
|---|---|---|
| 1-18 | Positive | Negative |
| 19-25 | Positive | Positive |

TABLE 4

Immunohistochemical results in histopathologically negative tissue biopsies (of the patients with continuous nos. 1 through 25, patients nos. 1 through 7 of PCR are included).

| Patient | Regular healthy intestinal mucosa |
|---|---|
| 1-6 | Negative |
| | Sigmoid diverticulitis |
| 7-18 | Negative |
| | Colorectal adenoma |
| 19-25 | Negative |

Results of the Proliferation Assay

Figure 2:
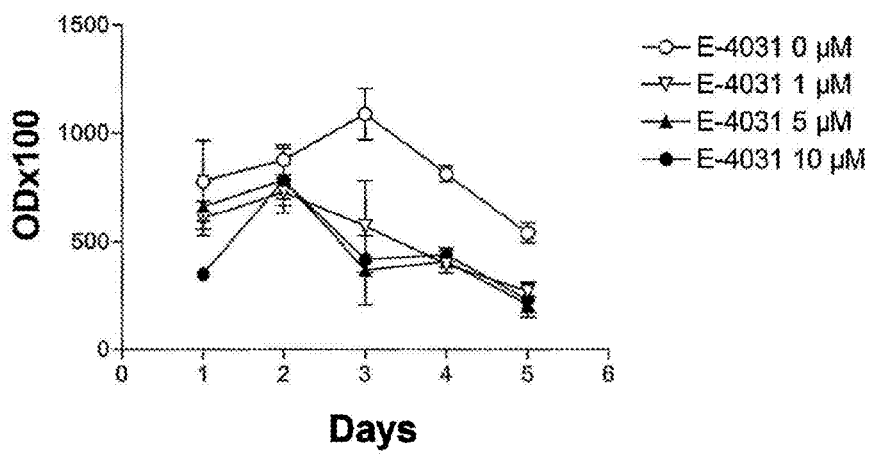
FIG. 2 is a series of 4 graphs depicting the inhibition of proliferation of the Colo-205 colorectal carcinoma cell line, at an initial inoculation of 10,000 cells per well by the selective inhibitor E-4031 of the HERG potassium channel, employing Compound E-4031 at 0 µM (control), 1 µM, 5 µM and 10 µM concentrations, respectively.

FIG. 2 shows the inhibition of proliferation of the Colo-205 colorectal carcinoma cell line by the selective inhibitor E-4031 of the HERG potassium channel.

E-4031 was supplied to the cells in three different concentrations (1, 5 and 10 µM) and then the growth response of the colorectal carcinoma cells was measured on the five following days. Growth of the carcinoma cells was inhibited by the concentrations of E-4031, due to the blocking of the HERG potassium channel, which is important for the growth of cancer, and then the cancer cells died off.

Thus according to the present invention, a tumor marker has been discovered which makes it possible to reliably differentiate cancerous (malignant) tissue from non-cancerous (benign) colorectal tissue and thus to detect cancer and also detect cancerous tumor cells in histopathologically unremarkable tissue. In colorectal adenomas, this is especially important for reliable early detection of carcinoma cells and for reliable detection of micrometastases in histopathologically unremarkable tissue, and in the lymph nodes it is important for the course of treatment and for the prognosis.

CEA is not suitable as such a marker because CEA mRNA has not been detected in stage I colorectal carcinomas but it is expressed in all tissue biopsies of tubulovillous colon adenomas and in two samples of sigmoid diverticulitis which functioned as negative controls. It is consistent with the findings presented here that Bhatnagar et al. found (by means of quantitative enzyme immunoassay and immunocytochemistry) that CEA is not present at all in moderately to slightly differentiated colorectal tumors. Boucher et al. demonstrated that CEA occurs not only in adenocarcinoma of the colon but also in healthy adjacent mucosal tissue of the colon.

CK-19 and CK-20 occur not only in serum but only in colorectal tissue so they are not reliable tumor markers. They cannot be detected in advanced stage III carcinoma, but they can be detected in some control tissue biopsies. This confirms previous observations that CK-19 and CK-20 can also be discovered in healthy intestinal mucosa but are not present in some tumors. The observation that the abundant occurrence of CK-19 in well-differentiated tumor tissue and in low-grade dysplasia with slight cellular proliferation as well as the low occurrence in slightly differentiated carcinoma tissue and in high-grade dysplasia with a high proliferation rate as well as the slight expression of CK-20 in colorectal carcinoma in comparison with healthy colon tissue all suggest that the negative tumor biopsies of stage III is in a high proliferation status. The contrary findings of the tissue biopsy from patient no. 2 (Table 1) additionally show that the markers are not distributed uniformly in the tumor.

In contrast with the findings for CEA, CK-19 and CK-20, HERG expression was found selectively in all colorectal carcinomas regardless of the tumor stage and was negative in all control tissue biopsies. This can be detected on a molecular biological level by detection of HERG RNA using the PCR method as well as by immunohistochemistry by detection of the HERG protein selectively in the colorectal carcinoma cells.

HERG-positive reactions were detected by immunohistochemical methods in some tumor patients In some histopathologically negative residual intestinal components of resected tissue from tumor patients. In the two years following surgical resection of the carcinoma, these patients experienced a locoregional recurrence of the colorectal carcinoma. This is a sign of micrometastases in histopathologically unremarkable colorectal tissue.

By detection of HERG with two sensitive independent methods, both of which are conventional, there is an enormous gain in the quality and reliability of detection results.

Therefore, the HERG potassium channel is a highly selective tumor marker for colorectal tissue.

It is also a valuable marker for other epithelial carcinomas because it also occurs in endometrial cancer. The data presented suggests a strong involvement of the EAG potassium channels, including the HERG potassium channel, which has recently been suspected on the basis of in vitro studies, in the carcinogenesis. These potassium channels have been found in various tumor cell lines which transfer a transformed phenotype into transfected cells of mammals and favor tumor progression in immunosuppressed mice. Since the HERG potassium channel is of immense important for tumor growth and/or survival of the tumor, proliferation studies have shown that by selective blockade of the HERG potassium channel by E-4031, the carcinoma cells are induced to die off. The HERG potassium channel as a functional tumor marker for colorectal carcinoma is thus not only a selective tumor marker but also permits a new approach for cancer therapy through selective inhibition of E-4031.

The surprising and valuable findings of this invention can be summarized by stating that a reliable diagnosis of colorectal carcinoma cells is possible by selective HERG gene expression in two independent test methods (immunohistochemistry and PCR) with a novel and highly selective marker being used in the form of the HERG potassium channel, and the growth of tumor cells being inhibited by the antiarrhythmic agent E-4031.

What is claimed is:

1. A method of treating a colorectal carcinoma having at least one voltage-activated potassium ion channel HERG subunit in a patient in need of said treatment, which comprises the step of administering to said patient a therapeutically effective amount of 4-[1-{2-(6-methyl-2-pyridinyl)ethyl-4-piperidinyl}carbonyl]methane-sulfoanilide 2HCl sufficient to treat the colorectal carcinoma having at least one voltage-activated potassium ion channel HERG subunit.

2. A method of treating colorectal carcinoma having at least one voltage-activated potassium ion channel HERG subunit in a patient in need of said treatment, which comprises the step of administering to said patient, a therapeutically effective amount of 4-[1-{2-(6-methyl-2-pyridinyl)ethyl-4-piperidinyl}carbonyl]methane-sulfoanilide 2HCl sufficient to treat the colorectal carcinoma having at least one voltage-activated potassium ion channel HERG subunit by selectively blockading the HERG subunit.

3. A method of treating colorectal carcinoma having at least one voltage-activated potassium ion channel HERG subunit in a patient defined in claim 2 wherein the colorectral carcinoma having at least one voltage-activated potassium ion channel HERG subunit is located in the colon, the sigmoid colon or the rectum.

* * * * *

SEQUENCE LISTING

<160> NUMBER OF SEQ ID NOS: 15

<210> SEQ ID NO 1
<211> LENGTH: 30
<212> TYPE: DNA
<213> ORGANISM: Homo sapiens

<400> SEQUENCE: 1
tctggaactt ctcctggttc tctcagctgg         30

<210> SEQ ID NO 2
<211> LENGTH: 30
<212> TYPE: DNA
<213> ORGANISM: Homo sapiens

<400> SEQUENCE: 2
tgtagctgtt gcaaatgctt taaggaagaa         30

<210> SEQ ID NO 3
<211> LENGTH: 25
<212> TYPE: DNA
<213> ORGANISM: Homo sapiens

<400> SEQUENCE: 3
gggccactgt cggcatcatg attgg              25

<210> SEQ ID NO 4
<211> LENGTH: 20
<212> TYPE: DNA
<213> ORGANISM: Homo sapiens

<400> SEQUENCE: 4
gtggaggtgg attccgctcc                    20

```
<210> SEQ ID NO 5
<211> LENGTH: 19
<212> TYPE: DNA
<213> ORGANISM: Homo sapiens

<400> SEQUENCE: 5
tggcaatctc ctgctccag                                                    19

<210> SEQ ID NO 6
<211> LENGTH: 20
<212> TYPE: DNA
<213> ORGANISM: Homo sapiens

<400> SEQUENCE: 6
atggccgagc agaaccggaa                                                   20

<210> SEQ ID NO 7
<211> LENGTH: 20
<212> TYPE: DNA
<213> ORGANISM: Homo sapiens

<400> SEQUENCE: 7
ccatgagccg ctggtactcc                                                   20

<210> SEQ ID NO 8
<211> LENGTH: 21
<212> TYPE: DNA
<213> ORGANISM: Homo sapiens

<400> SEQUENCE: 8
gcgtttatgg gggtgctgga g                                                 21

<210> SEQ ID NO 9
<211> LENGTH: 22
<212> TYPE: DNA
<213> ORGANISM: Homo sapiens

<400> SEQUENCE: 9
aaggctctgg gaggtgcgtc tc                                                22

<210> SEQ ID NO 10
<211> LENGTH: 18
<212> TYPE: DNA
<213> ORGANISM: Homo sapiens

<400> SEQUENCE: 10
cggcggggac ctgtttgt                                                     18

<210> SEQ ID NO 11
<211> LENGTH: 22
<212> TYPE: DNA
<213> ORGANISM: Homo sapiens

<400> SEQUENCE: 11
cagtgttgcc cagatgcttg tg                                                22

<210> SEQ ID NO 12
<211> LENGTH: 24
<212> TYPE: DNA
<213> ORGANISM: Homo sapiens

<400> SEQUENCE: 12
agctgatcgg gctgctgaag actg                                              24
```

```
<210> SEQ ID NO 13
<211> LENGTH: 25
<212> TYPE: DNA
<213> ORGANISM: Homo sapiens

<400> SEQUENCE: 13
aatgagcatg acgcagatgg agaag                                          25

<210> SEQ ID NO 14
<211> LENGTH: 24
<212> TYPE: DNA
<213> ORGANISM: Homo sapiens

<400> SEQUENCE: 14
ccacccatgg caaattccat ggca                                           24

<210> SEQ ID NO 15
<211> LENGTH: 24
<212> TYPE: DNA
<213> ORGANISM: Homo sapiens

<400> SEQUENCE: 15
tctagacggc aggtcaggtc cacc                                           24
```